(12) United States Patent
Wassermann et al.

(10) Patent No.: US 7,479,161 B1
(45) Date of Patent: *Jan. 20, 2009

(54) ARTIFICIAL URINARY DIVERSION SYSTEM

(76) Inventors: Helmut Wassermann, Struwwelpeterstrasse 5B, München (DE) D-81739; Dieter Jocham, Zwinglistrasse 1, Lübeck (DE) D-23568

( * ) Notice: Subject to any disclaimer, the term of this patent is extended or adjusted under 35 U.S.C. 154(b) by 0 days.

This patent is subject to a terminal disclaimer.

(21) Appl. No.: 09/936,721

(22) PCT Filed: Mar. 17, 2000

(86) PCT No.: PCT/EP00/02407

§ 371 (c)(1),
(2), (4) Date: Dec. 19, 2001

(87) PCT Pub. No.: WO00/56246

PCT Pub. Date: Sep. 28, 2000

(30) Foreign Application Priority Data

Mar. 18, 1999 (DE) ................. 199 12 218
Mar. 19, 1999 (DE) ................. 199 12 472

(51) Int. Cl.
*A61F 2/04* (2006.01)

(52) U.S. Cl. ................. 623/23.65; 623/23.68

(58) Field of Classification Search ................. 623/12, 623/23.64, 23.65, 11.11; 128/897
See application file for complete search history.

(56) References Cited

U.S. PATENT DOCUMENTS

| | | | |
|---|---|---|---|
| 3,796,221 A | 3/1974 | Hagfors | |
| 4,044,401 A * | 8/1977 | Guiset | 623/23.65 |
| 4,228,550 A | 10/1980 | Salkind | |
| 4,256,093 A | 3/1981 | Helms et al. | |
| 4,311,659 A * | 1/1982 | Rey et al. | 264/221 |
| 4,805,628 A | 2/1989 | Fry et al. | |
| 4,976,735 A | 12/1990 | Griffith et al. | |
| 5,041,136 A | 8/1991 | Wascher et al. | |
| 5,092,886 A * | 3/1992 | Dobos-Hardy | 623/23.65 |
| 5,147,388 A * | 9/1992 | Yamazaki | 623/3.13 |
| 5,304,114 A | 4/1994 | Cosman et al. | |
| 5,649,902 A | 7/1997 | Yoon | |

(Continued)

FOREIGN PATENT DOCUMENTS

DE  24 31 888 A1  1/1976

(Continued)

*Primary Examiner*—Corrine M McDermott
*Assistant Examiner*—Christopher D Prone
(74) *Attorney, Agent, or Firm*—Lerner, David, Littenberg, Krumholz & Mentlik, LLP (57) ABSTRACT

An artificial urinary diversion system is disclosed, which consists of a first area with at least one outlet, a second area, and a third area with at least one inlet for accommodating a urinary bladder. The second area is arranged between the first area and the third area, and that the cross-sectional surfaces of the first and/or second areas which are perpendicular to the axial alignment of the urinary diversion system are smaller than the cross-sectional surface of the third area, thereby providing a shape that can be adapted to almost any patient. These artificial urinary diversion systems provide adaptable systems that can be produced without previous direct or indirect determination of the potentially available volume for the system, and that facilitate an as effective as possible determination and utilization during the surgical phase of the volume available in the patient.

40 Claims, 11 Drawing Sheets

U.S. PATENT DOCUMENTS

| | | |
|---|---|---|
| 5,785,641 A | 7/1998 | Davis |
| 5,813,410 A * | 9/1998 | Levin .................. 128/897 |
| 6,212,430 B1 | 4/2001 | Kung |
| 6,324,430 B1 | 11/2001 | Zarinetchi et al. |
| 6,324,431 B1 | 11/2001 | Zarinetchi et al. |
| 6,366,814 B1 * | 4/2002 | Boveja et al. .................. 607/45 |

FOREIGN PATENT DOCUMENTS

| | | |
|---|---|---|
| DE | 27 14 810 A1 | 10/1977 |
| DE | 94 03 020.0 U1 | 5/1994 |
| EP | 0 445 782 A1 | 9/1991 |
| WO | WO 93/16659 | 9/1993 |
| WO | WO 95/11637 | 5/1995 |
| WO | WO 9511637 A1 * | 5/1995 |
| WO | WO 98/35633 | 8/1998 |

* cited by examiner

ARTIFICIAL URINARY DIVERSION SYSTEM

FIELD OF THE INVENTION

The present invention relates to an artificial urinary diversion system.

BACKGROUND OF THE INVENTION

Among patients with urinary bladder disorder there are a number of potential problems which require the removal of their bladders. In these situations, a urinary diversion, by producing different sorts of reservoirs, is required. So-called wet diversions are those with direct urinary diversion through the ureters, which are implanted into the abdominal wall, or by insertion of a neutralized portion of the intestine, in which the ureters are implanted, and which is for its part implanted into the abdominal wall.

In both cases the urine is collected in a urine bag, which is attached to an orifice.

Alternatively, the ureters are implanted into the rectum or—increasingly in the past few years—into replacement bladders, which are made of neutralized parts of the intestine.

These replacement bladders are either connected to the endogenous urethra, or they are conducted out of the body by creating an appropriate self-preserving occlusion mechanism at the abdominal skin, for example in the navel region.

Typical indicators for a replacement of the endogenous urinary bladder are advanced tumors in the urinary bladder, but there are also malformations, bladder impairments due to inflammation, as well as functional obstructions, such as obstructions by urinating, or development of bladder atrophies among paraplegics.

It is therefore one object of the present invention to create an artificial urinary diversion system, which is adaptable to the different shapes of different persons, and which presents the largest possible filling volume.

It is another object of the present invention to create artificial urinary diversion systems which are adaptable, without previous direct or indirect determination of the potentially available volume for said system such that as effective as possible a determination and utilization during the surgical phase of the volume available in the patient is facilitated.

SUMMARY OF THE INVENTION

In accordance with the present invention, these and other objects have now been realized by the invention of artificial urinary diversion apparatus extending in a longitudinal direction comprising a first area having a plurality of first cross-sectional areas perpendicular to the longitudinal direction and a first outer surface, a second area having a plurality of second cross-sectional areas perpendicular to the longitudinal direction and a second outer surface, and a third area having a plurality of third cross-sectional areas perpendicular to the longitudinal direction and a third outer surface, the second area being disposed between the first area and the third area, the first area including at least one outlet, the third area including at least one inlet, at least one of the plurality of first and second cross-sectional areas being smaller than at least of one of the plurality of third cross-sectional areas and at least one of the plurality of first cross-sectional areas being greater than at least one of the plurality of second cross-sectional areas, a sphincter mechanism for opening and closing the outlet, and control means for controlling the sphincter mechanism. Preferably, the first, second and third areas comprise a modular unit having the first, second and third outer surfaces adapted to provide a continuous outer surface for the apparatus.

In accordance with one embodiment of the artificial urinary diversion apparatus of the present invention, the apparatus includes fluid guide means for guiding a fluid directly from the third area to the first area through the second area.

In accordance with a preferred embodiment of the artificial urinary diversion apparatus of the present invention, the sphincter mechanism is disposed in the first area.

In accordance with another embodiment of the artificial urinary diversion apparatus of the present invention, the apparatus includes a sensor for sensing the filling level of the apparatus. Preferably, the apparatus includes alarm means for providing an alarm based on the filling level sensed by the sensor. Preferably, the alarm means comprises a sound or seismic alarm signal.

In accordance with another embodiment of the artificial urinary diversion apparatus of the present invention, the sensor is controlled by the nerves responsible for the control of the normal bladder.

In accordance with another embodiment of the artificial urinary diversion apparatus of the present invention, the outer surface of the apparatus comprising the first, second and third outer surfaces has a shape in a plane perpendicular to the longitudinal direction corresponding to the 6th polynomial function $$F(x)=A+a_1x+a_2x^2+a_3x^3+a_4x^4+a_5x^5+a_6x^6$$

wherein A is between 0 and 2, $a_1$ is between 0 and 8, $a_2$ is between 0 and −2, $a_3$ is between 0 and 1, $a_4$ is between 0 and −0.1, $a_5$ is between 0 and 0.003, and $a_6$ is between −0.00001 and 0 and x is between 0 and 22.

In accordance with another embodiment of the artificial urinary diversion apparatus of the present invention, the outer surface of the apparatus comprising the first, second and third outer surfaces as a shape in a plane parallel to the longitudinal direction which corresponds to the 6th polynomial function $$F(x)=A+a_1x+a_2x^2+a_3x^3+a_4x^4+a_5x^5+a_6x^6$$

wherein A is between 0 and 2, $a_1$ is between 0 and 8, $a_2$ is between 0 and −2, $a_3$ is between 0 and 1, $a_4$ is between 0 and −0.1, as is between 0 and 0.003, and $a_6$ is between −0.00001 and 0 and x is between 0 and 22.

Preferably, the first, second and third outer areas are integrally formed.

In accordance with the present invention, the second area, which is arranged between the first area and the third area, has a cross-sectional surface that is smaller than the cross-sectional surface of the third area. In this manner, a shape is provided which can be adapted to almost any patient, and more particularly, the largest possible filling volume can be provided. This is accomplished by the simultaneous observance of the medical preconditions, such as that the arteries and the intestine that after the operation pass laterally to the second area, and on which no pressure must be applied. Attention must be paid to the fact that, when a person is standing erect, the third area is arranged above the second and the first area. For example, if the first area has a larger cross-sectional surface than the second area, a so-called constriction is provided in the second area, which is necessary for the bypassing of arteries and/or the intestine and the kidneys, and a positional fixing with the first area is possible at the pubic bone (Symphysis Pubica).

In accordance with another embodiment of the present invention, the first, second and third areas are modularly compounded, or rendered modularly compoundable, and the respective transition surfaces between the individual areas are coordinated in a manner such that a continuous transition results. In this manner, the advantage is achieved that, according to the respective spatial condition of the patient, the individual areas of the urinary diversion system can be compounded. It will thus be possible to take optimal account of the anatomical conditions of the patient.

In accordance with another embodiment of the present invention, a fluid guide is provided, which extends from the urinary bladder to the outlet in the first area. This corresponds, to a large extent, to the natural anatomy, meaning that with a person who is standing erect, the lowest, first area can be connected directly with the existing urethra, without using additional connection elements between the urethra and the outlet in the first area, which could possibly result in further medical complications.

In accordance with another embodiment of the present invention, an actor, or actuator, or a pump is provided in the third area, in which case there is no need to provide an external pump, and, in view of the overall shape of the device, the first and second areas are not negatively influenced. Furthermore, in the embodiment where an actuator or a pump is provided in the third area, it is taken into account that the third area, in an optimal embodiment, is most likely to have the most space for integration of a pump without significantly, or negatively, influencing the overall shape.

In accordance with another embodiment of the present invention, the pump is formed as a telescope device. The advantage of this embodiment is that almost the entire volume of the third area can be used for filling the urinary bladder contained therein. Laboratory experiments have shown that almost the entire urinary bladder can be emptied with such a telescope device, without leaving any sediment in the urinary bladder.

In accordance with another embodiment of the present invention, the pump is formed as a lever pump. In this case, the advantage is that no complex mechanics are integrated thereinto, such as for the use of a telescope device in the third area.

In accordance with another embodiment of the present invention, the pump is formed as a screw pump. The advantage of this embodiment is that almost the total volume of the third area can be used for the urinary bladder. In addition, by using a screw pump, it is possible for screw pump to pulverize possible smaller urine crystals, so that these pulverized crystals can also be passed through a stenotic urethra.

In accordance with another embodiment of the present invention, a screw pump is also arranged in a manner such that it can possibly be displaced laterally to the fluid tube or duct. In this embodiment, the advantage can be achieved that an inlet and a lavage of the artificial urinary diversion system can be provided efficiently, as the fluid tube will be opened by moving the screw. This possibility concerning the inlet and the lavage of the artificial urinary diversion system can be very important in the field of spectroscopic examinations.

In accordance with another embodiment of the present invention, a sphincter mechanism is preferably provided in the first area. In this embodiment, there is an advantage in that almost total control of the urinary continency is possible. Control of the sphincter mechanism can, for example, also be initiated externally.

In accordance with another embodiment of the present invention, a control system is provided which regulates the sphincter mechanism. In this embodiment, the control system, which is also capable of assuming further procedures, can also regulate the opening and closing of the sphincter.

In accordance with another embodiment of the present invention, a sensor system is provided that controls the filling level of the urinary bladder. In this case, the person involved will be provided with a high degree of safety by using these artificial urinary bladders. This means that the person involved does not have to void the urinary bladder regularly and in short intervals, but can integrate with everyday life in the usual manner. If either a sound signal or a seismical signal is provided, which will result from a certain filling level of the bladder, the person to whom it is provided can move normally in everyday life. However, it should be recognized that at least a security regulation is installed in the sensor system. In this manner, if a certain period of time elapses, for example 8 to 12 hours, a signal should be sent to the person to void the bladder, independent of the filling level of the bladder. Furthermore, when controlling the filling level of the artificial bladder security can be provided, which is oriented towards the physiologically marginal conditions. In this manner, the artificial urinary diversion system operates similar to the function of the natural urinary bladder. Thus, with the urinary diversion system of the present invention, similar to natural processes, the body first signals the person that the urinary bladder should be emptied, then the bladder will be opened, the urine will be pressed or squeezed out, and the bladder will be closed again.

In accordance with another embodiment of the present invention, the sensor system is controlled by the nerves responsible for the urinary bladder. In that case, an almost natural feeling will be provided to the concerned person with this neurological solution. Thus, an exogenous signal, such as for example that produced by a sound signal or a seismical signal, will not be necessary.

In accordance with another embodiment of the present invention, a power supply is also provided in the urinary diversion system. In this manner, a compact urinary diversion device can be provided, which can for example first be integrated into the artificial urinary diversion system. However, the power supply can also be arranged separately, near the urinary diversion system in the patient, if, for reasons of space, a third area must be used, which does not allow an additional power supply.

In accordance with another embodiment of the present invention, an external recharge device provides the power supply, in which case the urinary diversion system can be provided with almost lifelong power. The charging of the counterpart of the external recharge device can be provided by the adapted counterpart, which can be charged transcutaneously in a wireless manner, at an adapted main support location, which is implanted subcutaneously.

Simple power transfer can be achieved, for example, by the recharge device cooperating inductively with the counterpart, with power being transferred inductively with frequencies tolerated by the body, for example 30 kHz.

In accordance with another embodiment of the present invention, the power supply is provided by primary batteries, which are integrated into the urinary diversion device. This embodiment of the urinary diversion device will work without any continuing maintenance, and the person concerned does not have to worry about the power supply.

It is also pointed out that, in case of a particular need, the power for the actor system and/or the sensor system can be transferred transcutaneously in a wireless manner by placing a suitable transfer device onto the skin. However, it is also necessary in that case that the controlling and providing can be executed by primary batteries as an additional power source. It is also possible that the total control and sensor system can be interrogated and started by means of external telemetrically.

In accordance with another embodiment of the present invention, an actor system is also integrated into the urinary diversion device. In this case, a completely independent system is once again provided, which only needs to be connected at the inlets or outlets with functional structures of the patient's urinary diversion system, and which can be implanted as one compact unit.

In accordance with another embodiment of the present invention, the third area is constructed bipartite or in two-part form with, dependent on the filling level of the urinary bladder, one part being able to move away from the other part. In this case, it is therefore possible to flexibly adjust the size of the urinary bladder and the filling level, in accordance with the person's particular requirements.

In accordance with another embodiment of the present invention, the urinary diversion device of the present invention includes two inlets in the third area, so that each ureter can be connected with the artificial urinary diversion systems. In this embodiment, it is thus not necessary to provide a further separate additional element, for example in a Y-shape, which can be used if it is advantageous that the urinary diversion device have only one inlet.

By providing one or more anti-reflux valves in the third area, reflux of the urine into the kidney can thus be stopped. This also prevents possible ascent of bacteria from the bladder up to the kidney.

In accordance with another embodiment of the present invention, a fixing element is provided which is easy to arrange and fix in the human body. If the fixing element is connected with the urinary diversion device by means of a dovetail joint, a tight or leak-proof connection can be constructed, and the fixing element can be kept in the body in order to later be connected at the right place with the urinary diversion device.

In accordance with another embodiment of the present invention, the fixing element is moveably fixed by means of a guidance system. In accordance with this embodiment, the urinary diversion device can, according to the anatomy of the person concerned, optimally be arranged and fixed. If the guide-rail system is also integrated into the third area, there are no rails available that are protruding the third area, which could possibly influence the arranging in the human body, or cause any functional or spatial inconvenience.

In accordance with another embodiment of the present invention, the fixing element includes a splay or expanding element, which may widen after implanting into the guide rails. In this case, a simple connection is provided, which can guarantee compatibility by the complete integration of the splay element into the fixing element.

In accordance with another embodiment of the present invention, the fixing element is formed with a biocompatible material, such as silicone. In this manner, a well-tolerated material is provided, but also the elasticity of the silicone and other materials are taken into account due to the splay movements of the splay element.

BRIEF DESCRIPTION OF THE DRAWINGS

Referring to the following detailed description, the artificial urinary diversion system will be described in detail, and, in turn, refers to the drawings, in which.

DETAILED DESCRIPTION

Figure 1:
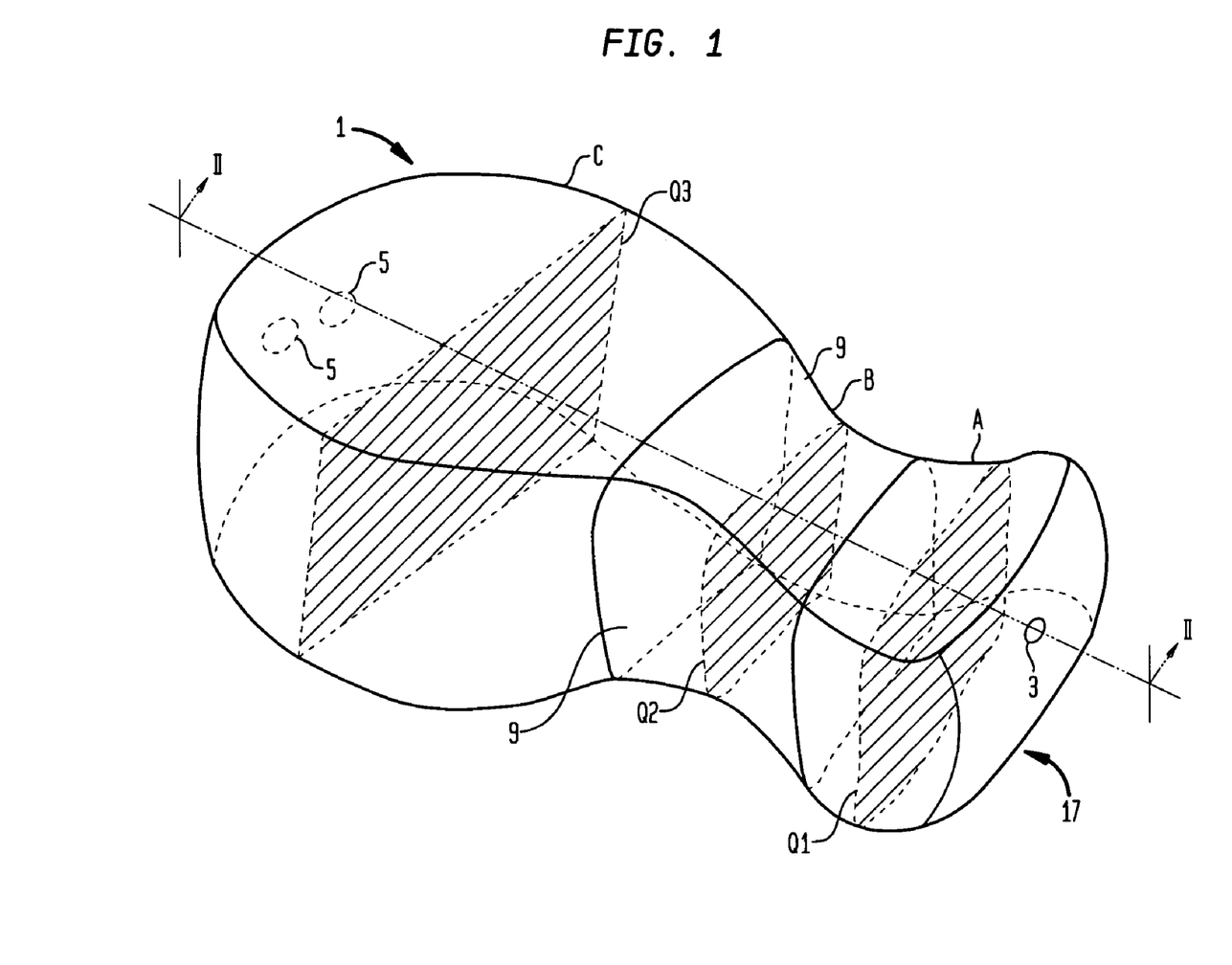
FIG. 1 is a side, perspective, schematic diagram of the artificial urinary diversion system of the present invention.

The particular embodiment of the urinary diversion system of the present invention set forth in FIG. 1 includes a first area A, a second area B and a third area C, with the cross-sectional surfaces (illustrated hatched) that are perpendicular to the axial alignment of the urinary diversion device of the first, second and third areas, being constructed such that the cross-sectional surface Q1 of the first area A is larger than the cross-sectional surface Q2 of the second area B and the cross-sectional surface Q3 of the third area C is in each case larger than the cross-sectional surface of the first and second areas. In addition, the first area A includes an outlet 3 and the third area C includes two inlets 5 for the urethras, which come from the respective kidneys.

The first area A of the urinary diversion system shows at its bottom surface 7 an increasing area D, with the shape possibly being linear, arched, concave or convex, dependent on the patient's anatomic conditions for the urinary diversion system. In FIG. 1 it can be clearly seen that the second area B, which is arranged between the first area and the third area, is to be regarded as a constriction, with arteries being lead laterally past its surfaces 9. The third area C, which comprises a urinary bladder, is shaped so as to be voluminous enough to allow for filling to as large a size as possible. The two inlets for the renal urethra are provided at the front side of the third area.

Figure 2:
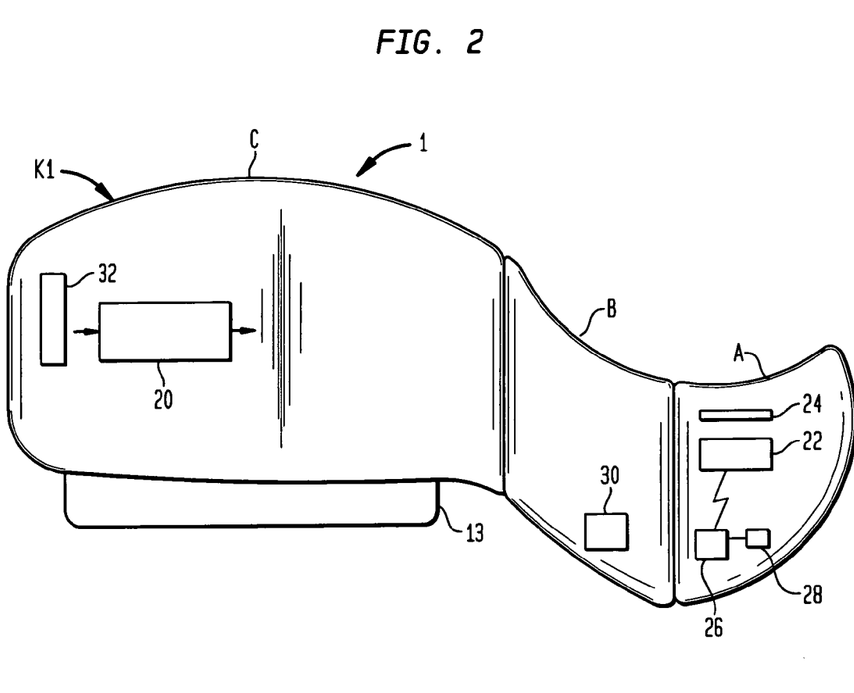
FIG. 2 is a side, elevational, sectional view of the artificial urinary diversion system of FIG. 1, taken along line II-II thereof.

FIG. 2 illustrates a laterally sectional view taken along line II-II. With this sectional view it is clearly seen that the urinary diversion device 1 presented in FIG. 2 shows the top-side of a first outline K1. Here, in contrast to FIG. 1, the elevation of the second area B to the bottom surface 7 of the first area A can be more clearly seen. In this embodiment, a curved or curvilinear elevation is shown. The curved elevation serves for being brought into contact, for example, with the pubic bone, thus makes positional fixing possible. It can also be seen in FIG. 2 that, below the third area, so-called guide rails 13 are provided, in which a fixing element (not shown) can be inserted. At this point, special attention shall be drawn to the fact that protruding of the guide rails may, for example, be avoided by complete integration into the third area.

Figure 3:
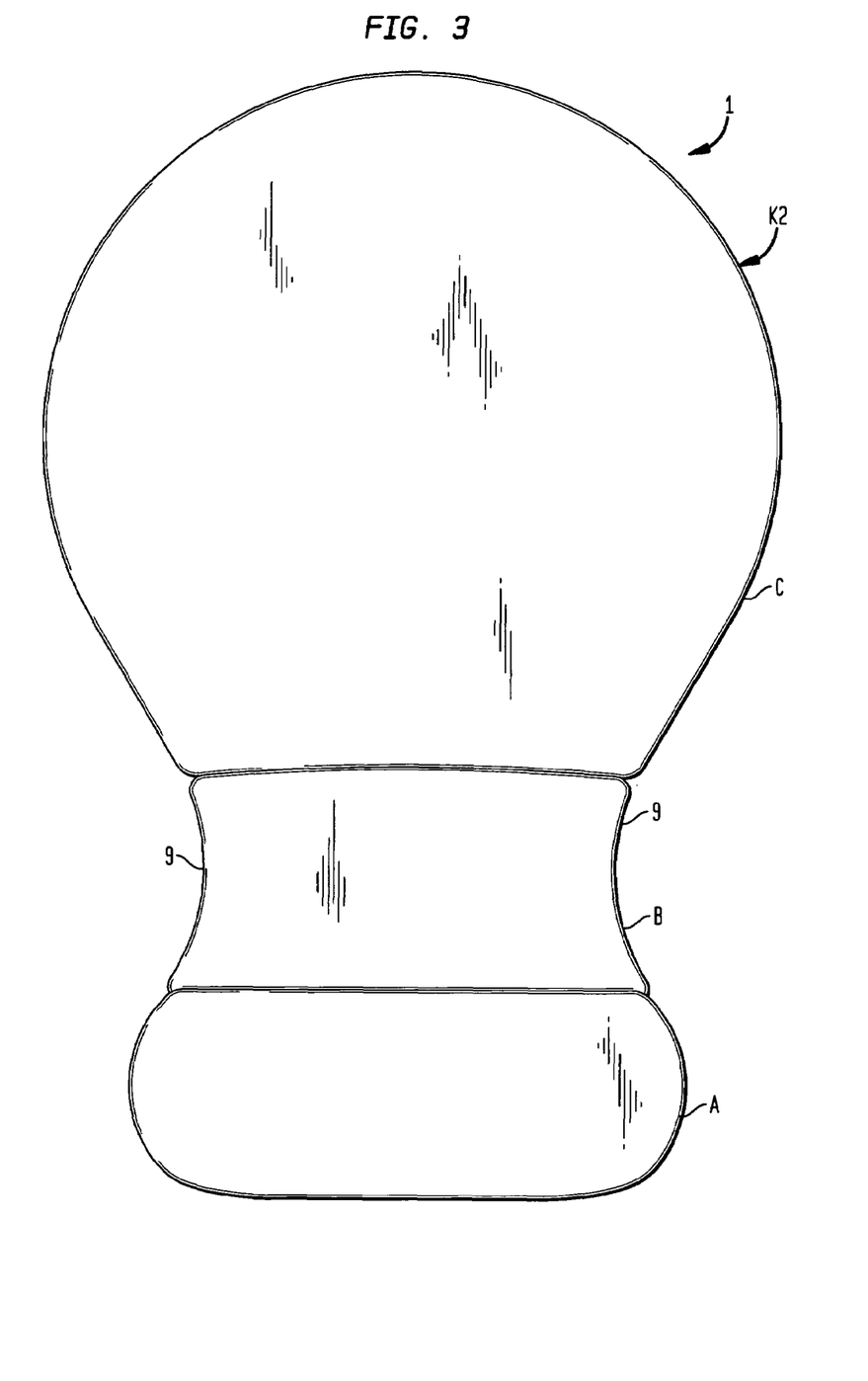
FIG. 3 is a top, elevational view of the urinary diversion system of FIG. 1.

FIG. 3 illustrates a top view of the urinary diversion system 1 and a second outline K2 in accordance with FIG. 1, with the constriction caused by the second area B being clearly visible, and with it being possible for the arteries to be lead laterally past the side surfaces 9. The relative proportions between the first, second and third areas are also clearly visible.

Figure 4:
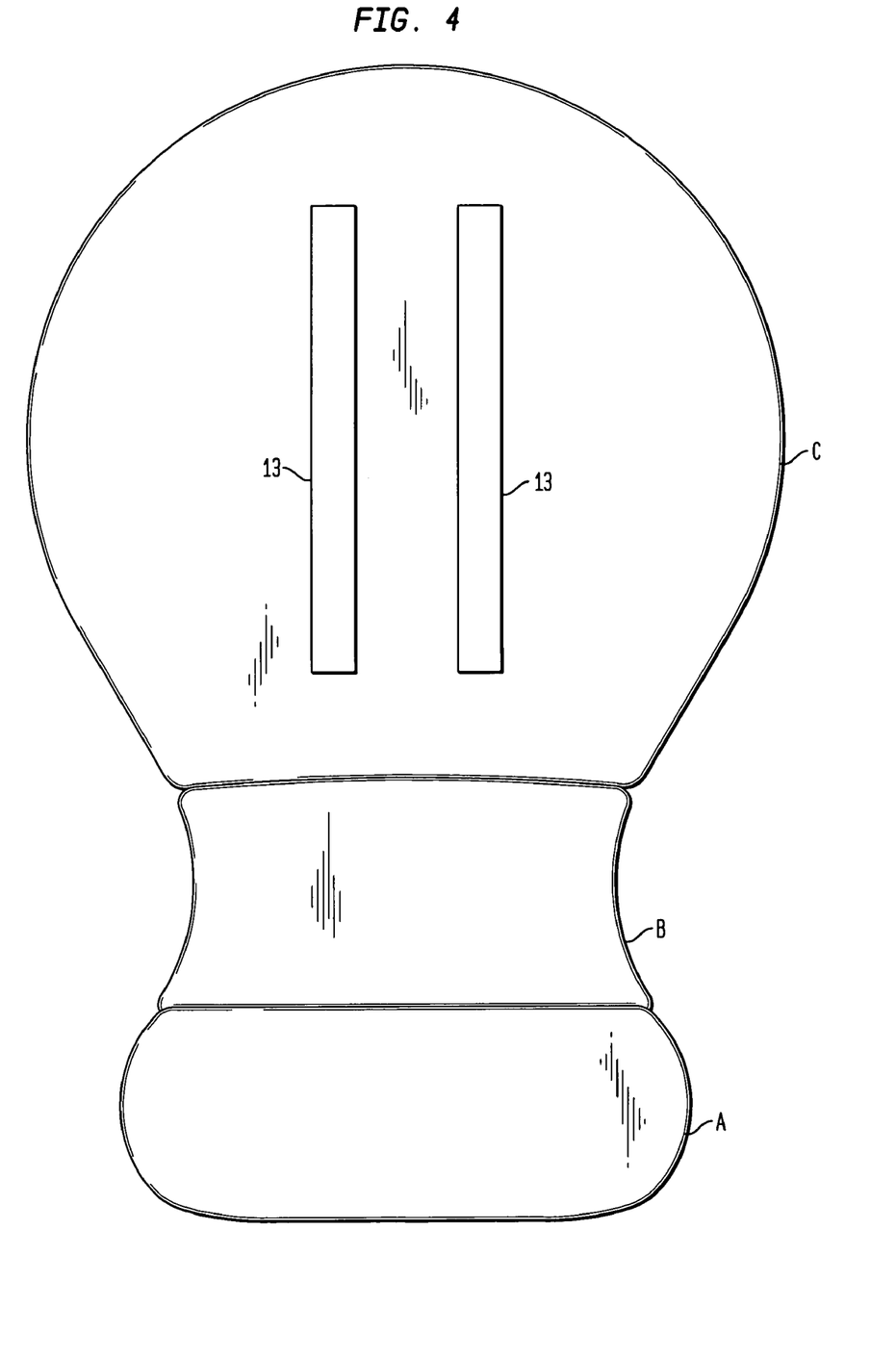
FIG. 4 is a bottom, elevational view of the urinary diversion system of FIG. 1.

FIG. 4 shows a bottom view of the urinary diversion system 1. The guide rails 13 which are provided for the fixing element are clearly indicated.

Figure 5:
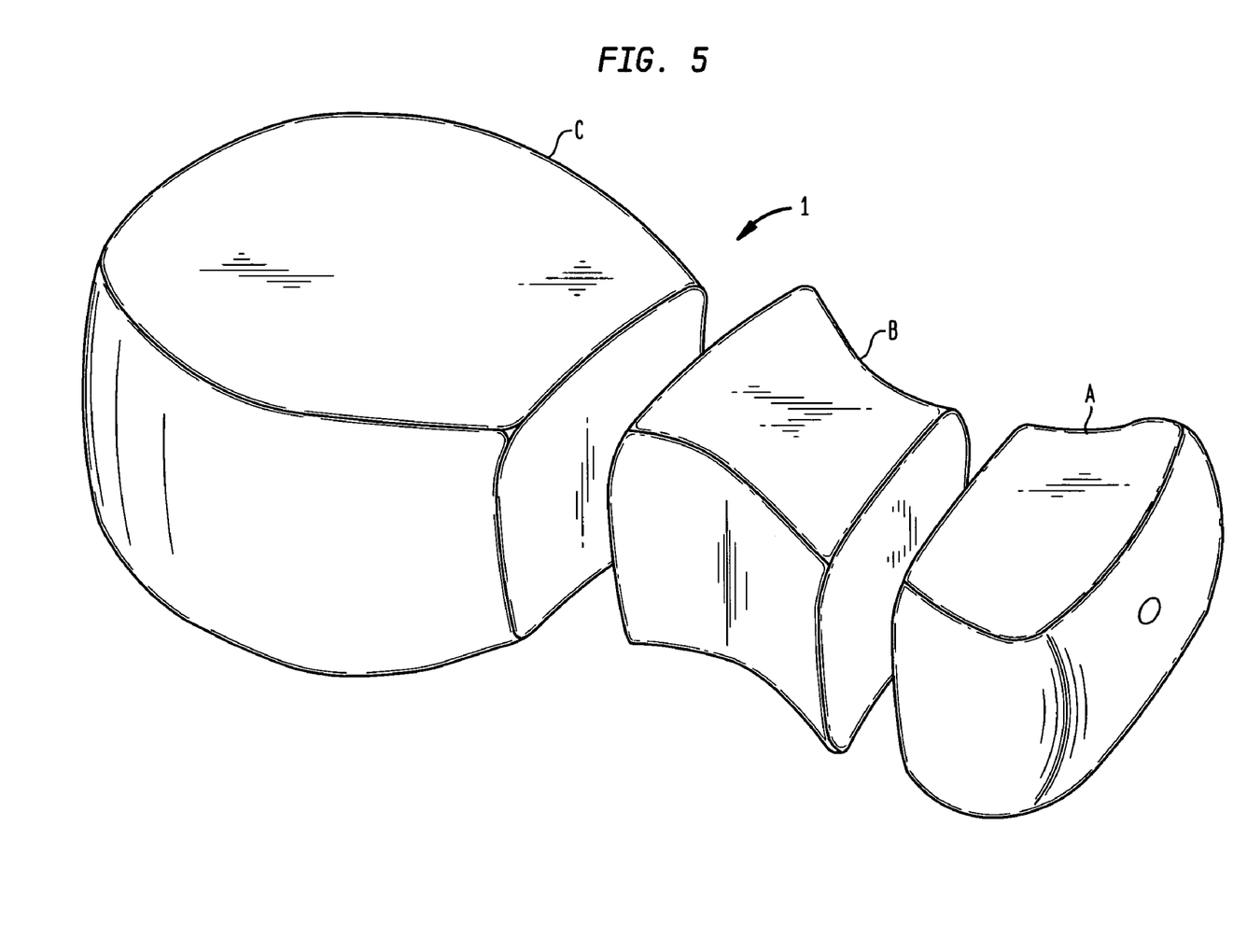
FIG. 5 is an exploded, side, perspective view of the urinary diversion system of FIG. 1.

FIG. 5 illustrates the urinary diversion system 1, with its individual areas, i.e., the first, second and third areas, illustrated separately.

It is also noted at this point that the division or sectioning into a first area, a second area and a third area describes a preferred embodiment. The urinary diversion system of the present invention can also be provided with only two areas or as an integral entity. On the other hand, more than three areas can also be provided, which can be divided separately, with more areas of the increased adapting variation being taken into account.

Figure 6:
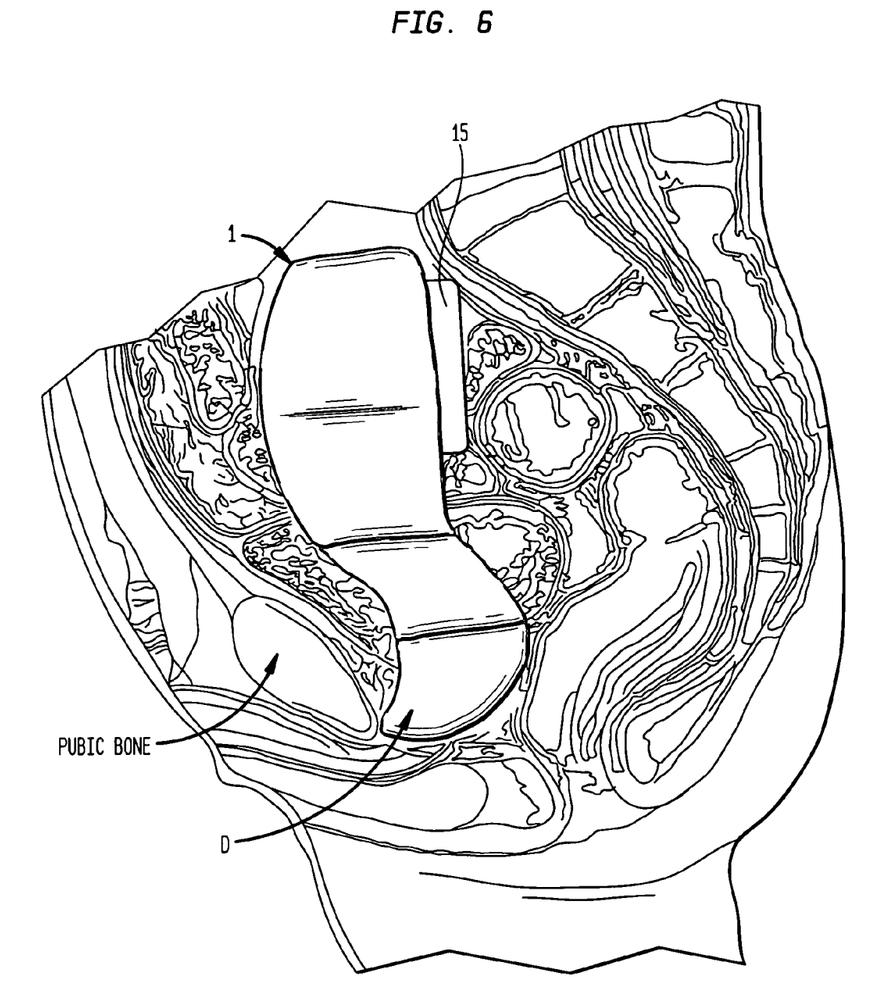
FIG. 6 is a side, elevational, sectional view of the urinary diversion system of FIG. 1, arranged in a body during use thereof.

FIG. 6 illustrates arrangement of the urinary diversion system of the present invention in a human body. The first area A borders on the pubic bone, with the fixing element, which is moveably includable in the guide rails, being fixed, for example, at the respective places in the abdominal cavity.

Figure 7:
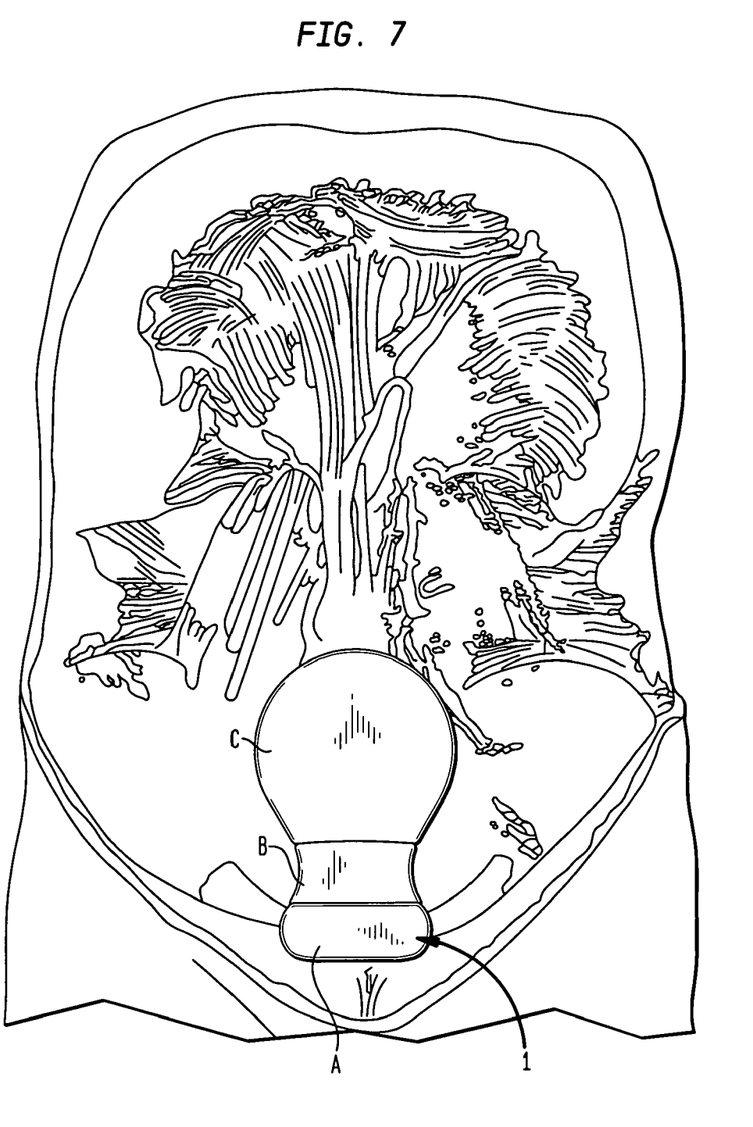
FIG. 7 is a front, elevational view of the urinary diversion system as shown in FIG. 1.

FIG. 7 shows a front view for further illustration of the arrangement of the urinary diversion system shown in FIG. 6.

Figure 8:
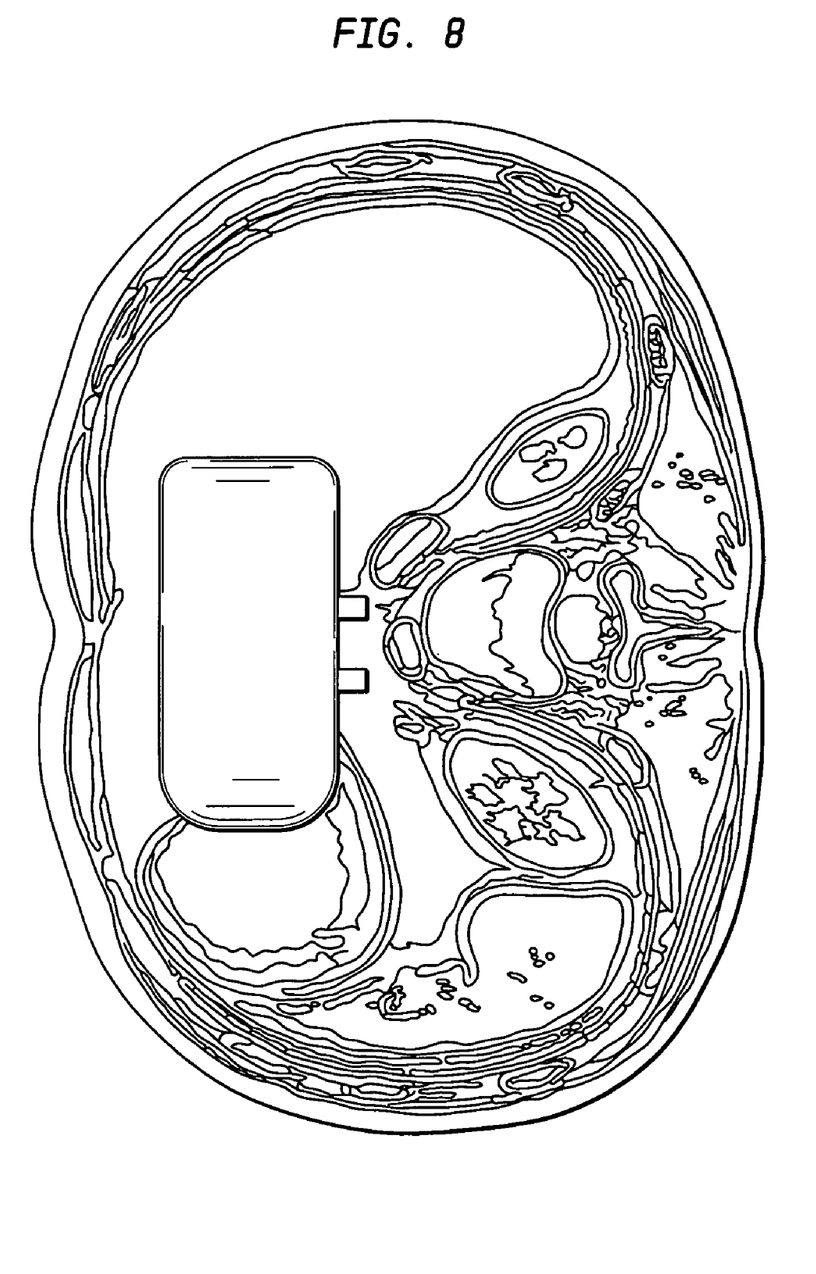
FIG. 8 is a top, elevational view of the urinary diversion system shown in FIG. 6, taken along line VII-VII thereof.

FIG. 8 is a top view, with the body section being above the section of the urinary diversion system.

Figure 9:
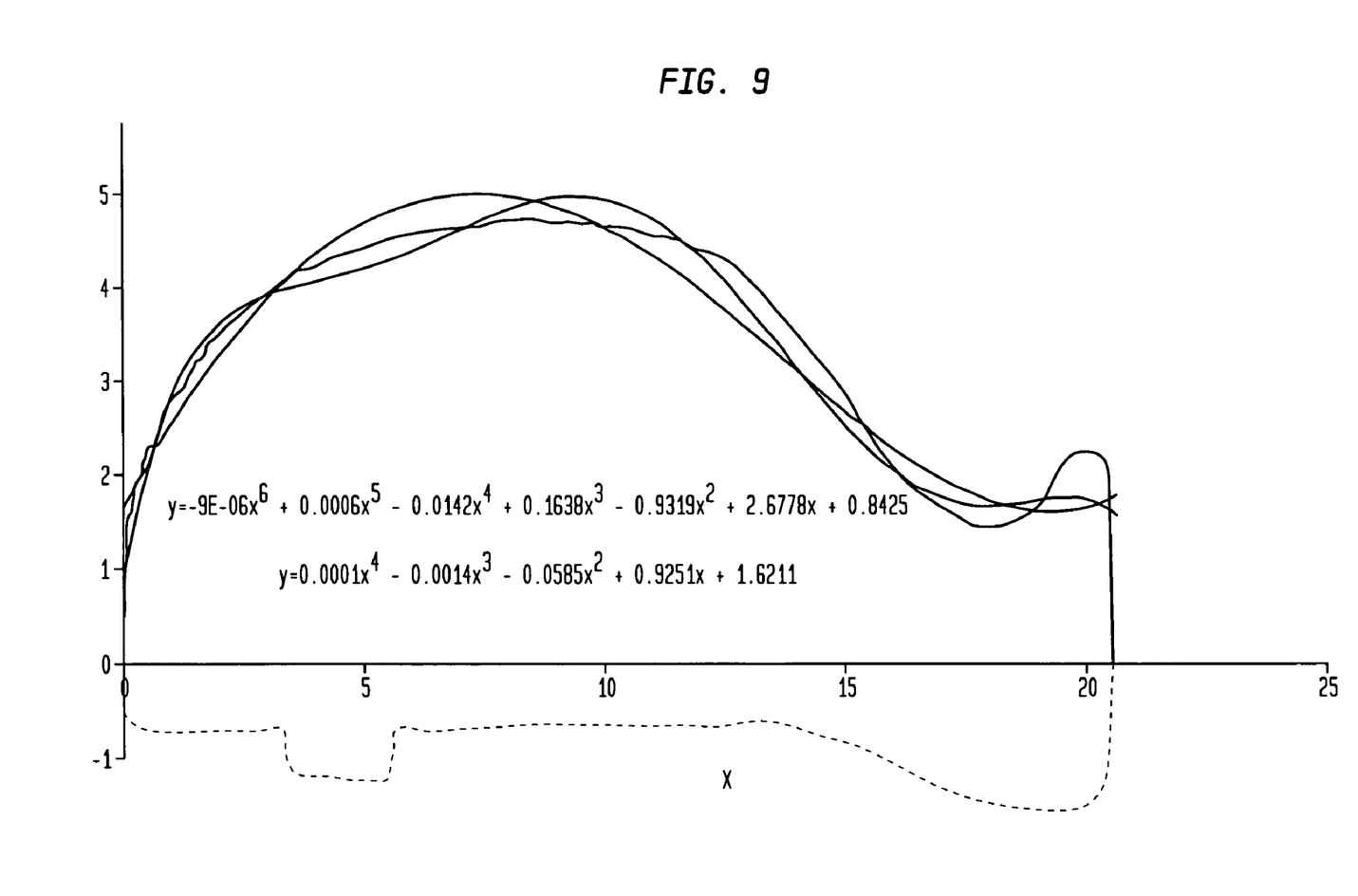
FIG. 9 is a graphical representation of one executed polynomial function of $6^{th}$ degree regarding the top surface outline of the urinary diversion system in accordance with FIG. 1.

FIG. 9 shows a fit curve of the polynomial form $f(x)=a_6x^6+a_5x^5+a_4x^4+a_3x^3+a_2x^2+a_1x+a$, i.e. a polynomial of $6^{th}$ degree, which has been adapted to the first outline. The parameters used for this adaptation are $a_6=-9\times10^6$; $a_5=0.006$; $a_4=-0.014$; $a_3=0.1638$; $a_2=-0.9319$; $a_1=2.6778$ and $a=0.8452$. However, within a domain of $0\leq X\leq 22$ the coefficients $a_1$ to $a_6$ in the domains $0<A<2$; $0<a_1<8$; $-2<a_2<0$; $0<a_3<1$; $-0,1<a_4<0$; $0<a_5<0,003$ and $-0,00001<a_6<0$, within a domain of $0\leq x\leq 22$, can be taken.

Figure 10:
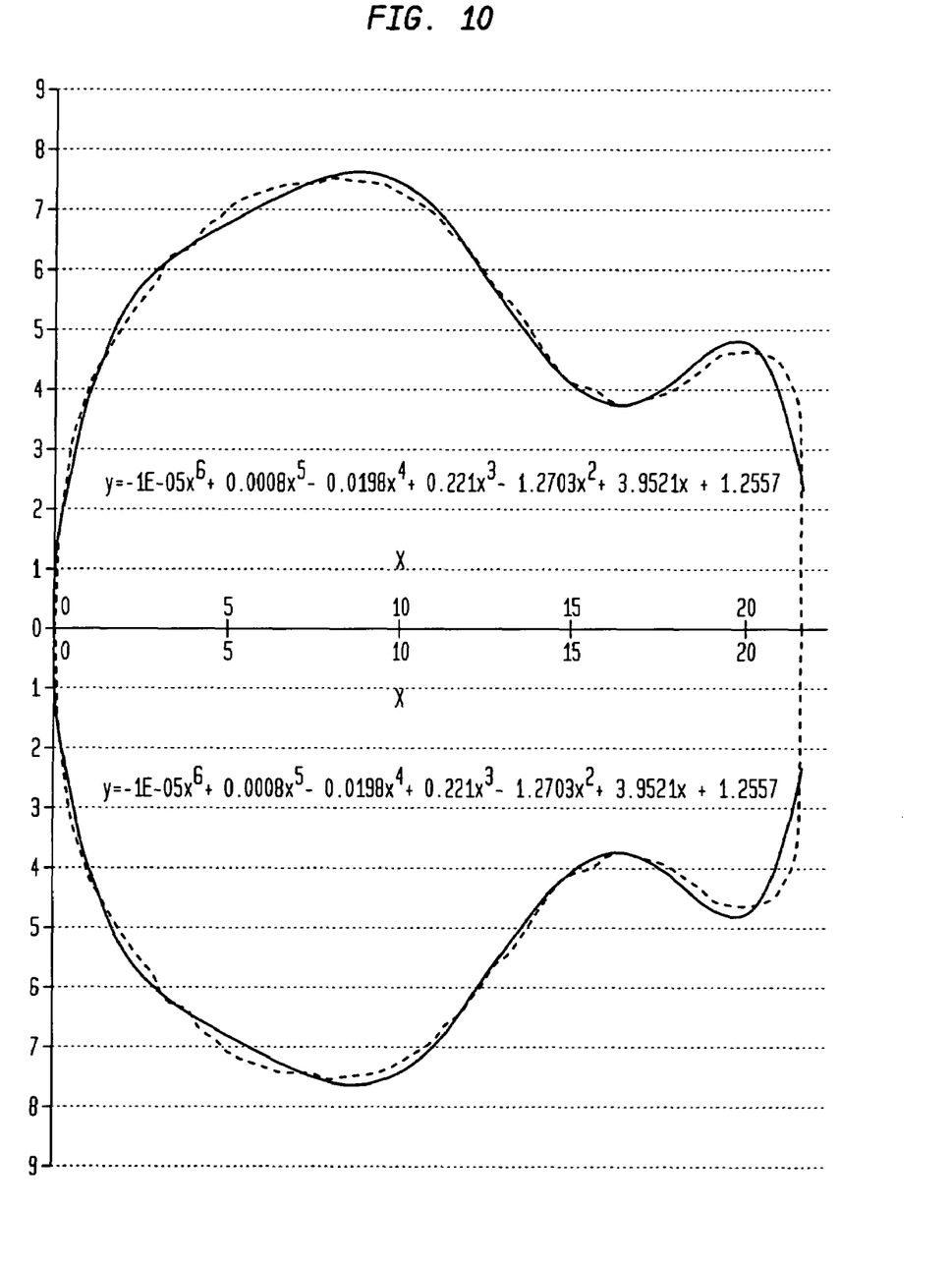
FIG. 10 is a graphical representation of the top-view silhouette of the urinary diversion system in accordance with FIG. 1, relating to the mentioned polynomial function of $6^{th}$ degree.

FIG. 10 illustrates a top view of the half of a second outline, which has also been approximated with a polynomial of $6^{th}$ degree. The parameters used for this adaptation are $a_6=1\times10^-5$; $a_5=0.008$; $a_4=-0.0198$; $a_3=0.221$; $a_2=-1.2703$; $a_1=3.9521$ and $A=1.2557$. These coefficients can also be taken in the domains $0<A<2$; $0<a_1<8$; $-2<a_2<0$; $0<a_3<1$; $-0,1<a_4<0$; $0<a_5<0,003$; and $-0,00001<a_6<0$ within a domain of $0\leq x\leq 22$, for adapting this second outline. To illustrate that FIG. 10 is a top view, the first outline and the fitted curve have been reflected at y=0 at the x-axis of the diagram.

Figure 11:
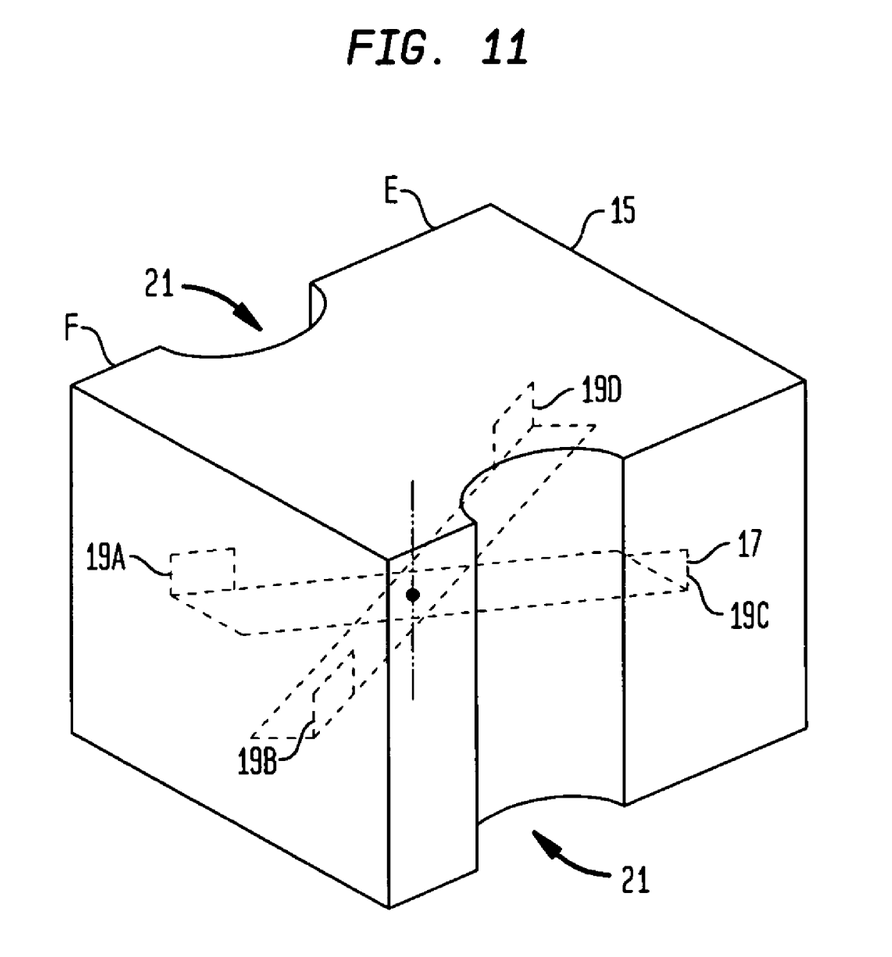
FIG. 11 is a side, perspective of an embodiment of the fixing element used with the urinary diversion system of the present invention.

FIG. 11 illustrates a fixing element 15 with a front area F, which can be introduced into the guide rails of the urinary diversion system of the present invention, and an end area E, which can, for example, be pressed by hand.

Inside of fixing element 15 there is a splay element (illustrated with dashed lines), which is, due to the upright side surfaces 19A to 19D, taken along with the elastically formed fixing element 15 in a manner so that, when impacting on the end area, the arms of the splay element 17 in the front area also move towards each other and take the elastic material of the fixing element 15 with them.

Thus, the fixing element 15 can be narrowed in such a manner that it can be included between the two guide rails 13. After introduction, the fixing element 15 be released, so that due to the elasticity of fixing element 15 the front area F will go back to its original shape, and a press fit/tight fit may be achieved with the side surfaces of the guide rails. If the fixing element 15 is then moved within the guide rail 13, it is only necessary to re-press or re-contract the end area E, in order to open the press fit of the side surfaces of the front area F. The slots or openings 21 in the fixing element 13 serve to be tightly led by the guide rails when the position of the fixing element might be re-aligned.

Thus, with this fixing element 15 the urinary diversion device of the present invention can be suitably arranged before its final disposition, and the fixing element can be fixed at the corresponding position in the abdominal cavity.

In accordance with this additional embodiment, in which a fixing element is provided which is separate from the urinary diversion system itself, it is also possible to pre-fix the fixing element at places which are difficult to access for fixing a fixing element, and to then introduce it into the urinary diversion device.

Instead of the screw pump, a pump using a telescope device, and a lever pump, various other types of pumps can be used for squeezing out the urine, particularly a membrane pump or a gear pump.

The cross-sectional surfaces Q1, Q2 and Q3 can be different geometrical surfaces, such as quadratic, rectangular, trapezoidal, round, oval, elliptical or any other combination thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Artificial urinary diversion apparatus extending in a longitudinal direction comprising a first portion having a plurality of first cross-sectional areas perpendicular to said longitudinal direction including at least one largest first cross-sectional area and a first outer surface, a second portion having a plurality of second cross-sectional areas perpendicular to said longitudinal direction including at least one largest second cross-sectional area and a second outer surface, and a third portion having a plurality of third cross-sectional areas perpendicular to said longitudinal direction including at least one largest third cross-sectional area and a third outer surface, said second portion being disposed between said first portion and said third portion, said first portion including at least one outlet, said third portion, said at least one largest first cross-sectional area being larger than said at least one largest second cross-sectional area, including at least one inlet, said at least one largest second cross-sectional area being smaller than said at least one largest third cross-sectional area, a sphincter mechanism for opening and closing said outlet, and control means for controlling said sphincter mechanism enclosed entirely within said artificial urinary diversion apparatus defined by said first, second and third outer surfaces.

2. The artificial urinary diversion apparatus of claim 1 including a sensor for sensing the filling level of said apparatus.

3. The artificial urinary diversion apparatus of claim 2 including alarm means for providing an alarm based on said filling level sensed by said sensor.

4. The artificial urinary diversion apparatus of claim 3 wherein said alarm means comprises a sound or seismic alarm signal.

5. The artificial urinary diversion apparatus of claim 2 wherein said sensor is controlled by the nerves responsible for the control of a normal bladder.

6. The artificial urinary diversion apparatus of claim 1 including a power supply.

7. The artificial urinary diversion apparatus of claim 6 wherein said power supply includes an external recharge device and an internal recharge responsive device cooperating with said external recharge device.

8. The artificial urinary diversion apparatus of claim 7 wherein said internal recharge responsive device cooperates inductively with said external recharge device.

9. The artificial urinary diversion apparatus of claim 6 wherein said power supply comprises primary battery means.

10. The artificial urinary diversion apparatus of claim 9 wherein said primary battery means is integrated into said apparatus.

11. The artificial urinary diversion apparatus of claim 1 including a fixing element for fixing said apparatus in a human body.

12. The artificial urinary diversion apparatus of claim 11 including connection means for connecting said fixing element to said apparatus.

13. The artificial urinary diversion apparatus of claim 12 wherein said connection means comprises a dovetail joint.

14. The artificial urinary diversion apparatus of claim 12 wherein said connection means comprises guide rail means for movably locking said fixing element at a predetermined location with respect to said apparatus.

15. The artificial urinary diversion apparatus of claim 14 wherein said guide rail means is integrated into said third area.

16. The artificial urinary diversion apparatus of claim 11 wherein said fixing element includes an expandable member for altering the shape of said fixing element.

17. The artificial urinary diversion apparatus of claim 16 wherein said expandable member is entirely included within said fixing member.

18. The artificial urinary diversion apparatus of claim 16 wherein said fixing element comprises a biocompatible elastic material.

19. The artificial urinary diversion apparatus of claim 18 wherein said biocompatible elastic material comprises silicone.

20. Artificial urinary diversion apparatus extending in a longitudinal direction comprising a first portion having a plurality of first cross-sectional areas perpendicular to said longitudinal direction including at least one largest first cross-sectional area and a first outer surface, a second portion having a plurality of second cross-sectional areas perpendicular to said longitudinal direction including at least one largest second cross-sectional area and a second outer surface, and a third portion having a plurality of third cross-sectional areas perpendicular to said longitudinal direction including at least one largest third cross-sectional area and a third outer surface, said second portion being disposed between said first portion and said third portion, said first portion including at least one outlet, said third portion including at least one inlet, said at least one largest second cross-sectional area being smaller than said at least one largest third cross-sectional area, a sphincter mechanism for opening and closing said outlet, and control means for controlling both the opening and closing of said sphincter mechanism enclosed entirely within said artificial urinary diversion apparatus defined by said first, second and third outer surfaces.

21. The artificial urinary diversion apparatus of claim 20 wherein said first, second and third portions are integrally formed.

22. The artificial diversion apparatus of claim 20 including a pump enclosed entirely within said artificial urinary diversion apparatus.

23. The artificial urinary diversion apparatus of claim 20 wherein each of said first, second and third areas comprises a modular unit having said first, second and third outer surfaces adapted to provide a continuous outer surface for said apparatus.

24. The artificial urinary diversion apparatus of claim 20 including fluid guide means for guiding a fluid directly from said third area to said first area through said second area.

25. The artificial urinary diversion apparatus of claim 20 including a pump.

26. The artificial urinary diversion apparatus of claim 25 wherein said pump is disposed in said third area.

27. The artificial urinary diversion apparatus of claim 26 wherein said pump comprises a telescopic pump.

28. The artificial urinary diversion apparatus of claim 26 wherein said pump comprises a lever pump.

29. The artificial urinary diversion apparatus of claim 28 wherein said lever pump is contained within two of said first, second and third areas.

30. The artificial urinary diversion apparatus of claim 26 wherein said pump comprises a screw pump.

31. The artificial urinary diversion apparatus of claim 30 wherein said screw pump is located within said first area.

32. The artificial urinary diversion apparatus of claim 31 wherein said screw pump comprises a plurality of screws, including at least one screw which is capable of being moved laterally.

33. The artificial urinary diversion apparatus of claim 20 wherein said sphincter mechanism is disposed in said first area.

34. The artificial urinary diversion apparatus of claim 20 including expulsion means for expelling liquid from said apparatus.

35. The artificial urinary diversion apparatus of claim 20 wherein said third area comprises a plurality of said third areas.

36. The artificial urinary diversion apparatus of claim 35 wherein said plurality of third areas are movably disposed with respect to each other.

37. The artificial urinary diversion apparatus of claim 20 wherein said third area includes a pair of said inlets.

38. The artificial urinary diversion apparatus of claim 20 including at least one anti-reflux valve.

39. The artificial urinary diversion apparatus of claim 38 including a plurality of said anti-reflux valves.

40. The artificial urinary diversion apparatus of claim 38 wherein said anti-reflux valve is contained within said third area.

* * * * *